US010954184B2

(12) United States Patent
Low et al.

(10) Patent No.: US 10,954,184 B2
(45) Date of Patent: Mar. 23, 2021

(54) FLUORINATED ESTERS AS LUBRICANTS FOR HEAT TRANSFER FLUIDS

(71) Applicant: MEXICHEM FLUOR S.A. DE C.V., San Luis Potosi (MX)

(72) Inventors: Robert Elliot Low, Cheshire (GB); Andrew Paul Sharratt, Cheshire (GB); Emma Jane Hodgson, Stoke-on-Trent (GB)

(73) Assignee: MEXICHEM FLUOR S.A. DE C.V., San Luis Potosi (MX)

( * ) Notice: Subject to any disclaimer, the term of this patent is extended or adjusted under 35 U.S.C. 154(b) by 0 days.

(21) Appl. No.: 15/781,415

(22) PCT Filed: Dec. 7, 2016

(86) PCT No.: PCT/GB2016/053846
§ 371 (c)(1),
(2) Date: Jun. 4, 2018

(87) PCT Pub. No.: WO2017/098234
PCT Pub. Date: Jun. 15, 2017

(65) Prior Publication Data
US 2018/0362441 A1    Dec. 20, 2018

(30) Foreign Application Priority Data
Dec. 7, 2015  (GB) ..................................... 1521524

(51) Int. Cl.
*C07C 69/63*   (2006.01)
*C09K 5/04*    (2006.01)
*C10M 171/00*  (2006.01)
*C10M 131/12*  (2006.01)
*C10N 10/10*   (2006.01)
(Continued)

(52) U.S. Cl.
CPC .............. *C07C 69/63* (2013.01); *C09K 5/045* (2013.01); *C10M 131/12* (2013.01); *C10M 171/008* (2013.01); *C09K 2205/126* (2013.01); *C10M 2201/062* (2013.01); *C10M 2203/024* (2013.01); *C10M 2207/023* (2013.01); *C10M 2207/026* (2013.01); *C10M 2207/042* (2013.01); *C10M 2207/2835* (2013.01); *C10M 2209/1033* (2013.01); *C10M 2211/02* (2013.01); *C10M 2211/024* (2013.01); *C10M 2211/044* (2013.01); *C10M 2211/0406* (2013.01); *C10M 2211/0445* (2013.01); *C10M 2213/02* (2013.01); *C10M 2215/04* (2013.01); *C10M 2223/04* (2013.01); *C10M 2223/043* (2013.01); *C10N 2010/10* (2013.01); *C10N 2020/099* (2020.05); *C10N 2020/101* (2020.05); *C10N 2020/103* (2020.05); *C10N 2030/08* (2013.01); *C10N 2040/30* (2013.01)

(58) Field of Classification Search
CPC ............ C10M 2215/04; C10M 131/12; C10M 171/008; C10M 2201/062; C10M 2203/024; C10M 2207/023; C10M 2207/026; C10M 2207/042; C10M 2207/2835; C10M 2209/1033; C10M 2211/02; C10M 2211/024; C10M 2211/0406; C10M 2211/044; C10M 2211/0445; C10M 2213/02; C10M 2223/04; C10M 2223/043; C10N 2260/08; C10N 2210/05; C10N 2220/301; C10N 2220/302; C10N 2220/303; C10N 2230/08; C10N 2240/30; C07C 69/63; C09K 2205/126; C09K 5/045
See application file for complete search history.

(56) References Cited

U.S. PATENT DOCUMENTS 5,486,302 A  *  1/1996  Short ..................... C09K 5/045
                                                   508/485
1,026,673 A1    4/2019  Low
(Continued)

FOREIGN PATENT DOCUMENTS

JP    H08269342    10/1996
JP    H10168383    6/1998
(Continued)

OTHER PUBLICATIONS

Baek, Jin-Wook et al., "Synthesis of partially fluorinated polyol esters and their lubrication properties," *Korean Society of Industrial and Engineering Chemistry*, 13(8):799-803, XP002767933 (2002).
Faurote, P. D., et al., "Partially Fluorinated Esters and Ethers as Temperature-Stable Liquids," *Industrial & Engineering Chemistry*, 48(3):445-454, XP55003173 (1956).
Gavryushin, E. V., et al., "Hydrophobicity and thermal stability of fluorinated pentaerythritol esters," *Russian Journal of Applied Chemistry*, 79(5):861-864, XP019406762 (2006).
(Continued)

*Primary Examiner* — Mark Kopec
*Assistant Examiner* — Jaison P Thomas
(74) *Attorney, Agent, or Firm* — Brinks Gilson & Lione; Yuezhong Feng

(57) ABSTRACT

The present invention provides compounds of formula (I): wherein W is independently selected from the group consisting of H, F, Cl, Br and I; 10 X is independently selected from the group consisting of H, F, Cl, Br, I, CW$_3$ and OR on the basis that at least one X is OR; R is independently selected from the group consisting of C(O) (CH$_2$)$_m$(CF$_2$)$_n$Y and CW$_2$C(CW$_2$OC(O)(CH$_2$)m(CF$_2$)nY)$_3$; m is an integer from 0 to 2; 15 n is an integer from 2 to 8; Y is C(Z)$_3$; and Z is independently selected from the group consisting of H, F, Cl, Br and I. Such compounds may be utilised as lubricants, for example in heat transfer compositions.

54 Claims, No Drawings

(51) Int. Cl.
*C10N 20/00* (2006.01)
*C10N 30/08* (2006.01)
*C10N 40/30* (2006.01)

(56) References Cited

U.S. PATENT DOCUMENTS

| | | | | |
|---|---|---|---|---|
| 10,266,736 | B2* | 4/2019 | Low | C08J 9/149 |
| 2013/0193369 | A1* | 8/2013 | Low | C08J 9/149 |
| | | | | 252/68 |
| 2016/0002519 | A1* | 1/2016 | Low | C08J 9/149 |
| | | | | 62/77 |

FOREIGN PATENT DOCUMENTS

| | | |
|---|---|---|
| JP | 2010/209045 | 9/2010 |
| RU | 2492055 C1 | 9/2013 |
| WO | WO 93/11098 | 6/1993 |
| WO | WO 2012/006206 A2 | 1/2012 |
| WO | WO 2016/064585 | 4/2016 |

OTHER PUBLICATIONS

Gorbunova, T. I., et al., "Antifrictional properties of fluorine-containing polyol esters," XP002767934 and XP055350168, Retrieved from the Internet on Feb. 28, 2017, http://notes.fluorinel.ru/public/pdfs/80 3.pdf (2012).

Gorbunova, T. I., et al., "Resistance of polyfluorinated complete esters of polyhydric alcohols to thermal oxidation: Comparison with nonfluorinated analogs," *Russian Journal of General Chemistry*, 76(11):1795-1800, XP019468087 (2006).

International Search Report and Written Opinion for International Application No. PCT/GB2016/053846, 13 pages (dated Mar. 20, 2017).

Pervova, M.G., et al., "Synthesis and GC-MS study of fluorinated esters derived from thrimethylolpropane," *Russian Journal of General Chemistry*, 78(9):1701-1706, XP55350156, (2008).

Scott, Timothy C., et al., "Two-component absorption/phase separation chemical heat pump to provide temperature amplification to waste heat streams," retrieved from STN Database Accession No. 1989:481434, XP002767935 (1989).

Shinoda, Kozo, et al., "Critical Composition in Liquid Mixtures of Components of Very Different Molar Volumes," *J. Phys. Chem.*, 65(10):1885-1886, XP55350154 (1961).

* cited by examiner

FLUORINATED ESTERS AS LUBRICANTS FOR HEAT TRANSFER FLUIDS

REFERENCE TO EARLIER FILED APPLICATIONS

This application is a 371 national phase of PCT/GB2016/053846, filed Dec. 7, 2016, and of GB Application No. 1521524.7, filed Dec. 7, 2015, the disclosures of which are incorporated, in their entirety, by this reference.

TECHNICAL FIELD OF THE INVENTION

The present invention relates to multi-ester compounds and to uses of and methods of preparing the same.

BACKGROUND OF THE INVENTION

The listing or discussion of information or a prior-published document in this specification should not necessarily be taken as an acknowledgement that the information or document is part of the state of the art or is common general knowledge.

Fluorocarbon-based compounds are currently used in a large number of commercial and industrial applications, such as propellants, blowing agents and heat transfer fluids. The interest in and use of fluorine-based compounds, particularly (hydro)fluoroolefins, as heat transfer fluids has increased as new refrigerants are sought.

Dichlorodifluoromethane (refrigerant R-12) possessed a suitable combination of refrigerant properties and was for many years the most widely used refrigerant. Due to international concern that fully and partially halogenated chlorofluorocarbons, such as dichlorodifluoromethane and chlorodifluoromethane, were damaging the earth's protective ozone layer, there was general agreement that their manufacture and use should be severely restricted and eventually phased out completely. The use of dichlorodifluoromethane was phased out in the 1990's.

Chlorodifluoromethane (R-22) was introduced as a replacement for R-12 because of its lower ozone depletion potential. Following concerns that R-22 is a potent greenhouse gas, its use is also being phased out. R-410A and R-407 (including R-407A, R-407B and R-407C) have been introduced as a replacement refrigerant for R-22. However, R-22, R-410A and the R-407 refrigerants all have a high global warming potential (GWP, also known as greenhouse warming potential).

1,1,1,2-tetrafluoroethane (refrigerant R-134a) was introduced as a replacement refrigerant for R-12. However, despite having a low ozone depletion potential, R-134a has a GWP of 1430. It would be desirable to find replacements for R-134a that have a lower GWP.

R-152a (1,1-difluoroethane) has been identified as an alternative to R-134a. It is somewhat more efficient than R-134a and has a greenhouse warming potential of 120. However the flammability of R-152a is judged too high, for example to permit its safe use in mobile air conditioning systems. In particular its lower flammable limit in air is too low, its flame speeds are too high, and its ignition energy is too low.

(Hydro)fluoroolefins, particularly tetrafluoropropenes, have been proposed as possible refrigerants for use in a variety of heat transfer devices.

Heat transfer fluids are often used in combination with lubricants, such as in heating and refrigeration systems. Such lubricants are included in heat transfer compositions to ensure continued smooth operation of the heat transfer system.

It is necessary that lubricants used in heat transfer compositions are compatible with the refrigerants in the compositions. The compatibility of the lubricant and the refrigerant is predicated on a number of factors, such as a desire for at least partial miscibility at part of the operating temperature range, a low tendency to degrade or react in use and appropriate viscosities for the application.

There is, therefore, a need for lubricants that can be used in conjunction with heat transfer fluids, both those currently used and those proposed as replacement compositions. In particular, lubricants are desired that are miscible with a wide range of heat transfer fluids, possess an appropriate viscosity, do not reduce the performance of heat transfer fluids and have low flammability; all in addition to successfully functioning as a lubricant.

Lubricants with low flammability are particularly important for heat transfer fluids that are used in automobile air-conditioning, as such compositions are in danger of coming into contact with hot metal surfaces of the engine.

DETAILED DESCRIPTION

The subject invention addresses the above and other deficiencies by the provision of a compound of formula (I):

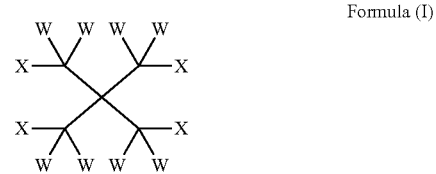

Formula (I)

wherein

W is independently selected from the group consisting of H, F, Cl, Br and I;

X is independently selected from the group consisting of H, F, Cl, Br, I, $CW_3$ and OR on the basis that at least one X is OR;

R is independently selected from the group consisting of $C(O)(CH_2)_m(CF_2)_nY$ and $CW_2C(CW_2OC(O)(CH_2)_m(CF_2)_nY)_3$;

m is an integer from 0 to 2;

n is an integer from 2 to 8;

Y is $C(Z)_3$; and

Z is independently selected from the group consisting of H, F, Cl, Br and I.

Further provided by the invention is a lubricant composition, and uses thereof, wherein the composition comprises a compound of formula (I).

Also provided by the invention is a heat transfer composition, and uses thereof, wherein the heat transfer composition comprises a heat transfer portion, together with one or more compounds of formula (I).

Further provided by the invention is a method of preparing a compound of formula (I) comprising reacting a compound of formula (A) with a compound of formula (B):

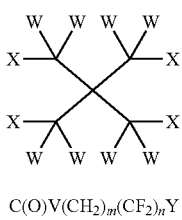

Formula (A)

$C(O)V(CH_2)_m(CF_2)_nY$

Formula (B)

wherein
W is independently selected from the group consisting of H, F, Cl, Br and I;
X is independently selected from the group consisting of H, F, Cl, Br, I, $CW_3$ and R, on the basis that at least one X is OR;
R is independently selected from the group consisting of H and $CW_2C(CW_2OH)_3$;
m is an integer from 0 to 2;
n is an integer from 2 to 8;
V is OH, F, Cl, Br or I;
Y is $C(Z)_3$; and
Z is independently selected from the group consisting of H, F, Cl, Br and I.

Compounds of the Invention

In one aspect, the invention provides a compound of formula (I):

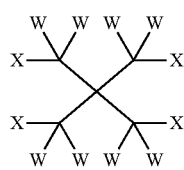

Formula (I)

wherein
W is independently selected from the group consisting of H, F, Cl, Brand I;
X is independently selected from the group consisting of H, F, Cl, Br, I, $CW_3$ and OR on the basis that at least one X is OR;
R is independently selected from the group consisting of $C(O)(CH_2)_m(CF_2)_nY$ and $CW_2C(CW_2OC(O)(CH_2)_m(CF_2)_nY)_3$;
m is an integer from 0 to 2;
n is an integer from 2 to 8;
Y is $C(Z)_3$; and
Z is independently selected from the group consisting of H, F, Cl, Br and I.

Such compounds show excellent resistance to ignition, including when exposed to hot surfaces.

In an embodiment, two of the X substituents are OR and the other two X substituents are, preferably, H. Preferably W is H. Advantageously, R is $C(O)(CH_2)_m(CF_2)_nY$. Preferably, m is and integer of 0 or 1, for example, 0. Favourably, n is an integer from 5 to 8, such as 5 or 6. Preferably, when m is 0, n is an integer of 5 or 6. Alternatively, when m is 1, n is an integer from 4 to 7. Preferably, Y is $C(Z)_3$, wherein, Z is advantageously H or F. Advantageously, Z is $CF_3$ or $CF_2H$.

In a further embodiment, two of the X substituents are OR and the other two X substituents are, preferably, H. Preferably W is H. Advantageously, R is independently selected from the group consisting of $C(O)(CF_2)_5CF_3$, $C(O)(CF_2)_5CF_2H$ and $C(O)(CF_2)_6CF_3$.

In an alternative embodiment, three of the X substituents are OR and the other X substituent is $CW_3$, preferably W is H. Advantageously, R is $C(O)(CH_2)_m(CF_2)_nY$. Preferably, m is and integer of 0 or 1, for example, 0. Favourably, n is an integer from 5 to 8, such as 5 or 6. Preferably, when m is 0, n is an integer of 5 or 6. Alternatively, when m is 1, n is an integer from 4 to 7. Preferably, Y is $C(Z)_3$, wherein, Z is advantageously H or F. Advantageously, Z is $CF_3$ or $CF_2H$.

In a further embodiment, three of the X substituents are OR and the other X substituent is $CW_3$, preferably W is H. Advantageously, R is independently selected from the group consisting of $C(O)(CF_2)_5CF_3$, $C(O)(CF_2)_5CF_2H$ and $C(O)(CF_2)_6CF_3$.

In an embodiment, all four of the X substituents are OR and, preferably, W is H. Advantageously, R is $C(O)(CH_2)_m(CF_2)_nY$. Preferably, m is and integer of 0 or 1, for example, 0. Favourably, n is an integer from 5 to 8, such as 5 or 6. Preferably, when m is 0, n is an integer of 5 or 6. Alternatively, when m is 1, n is an integer from 4 to 7. Preferably, Y is $C(Z)_3$, wherein, Z is advantageously H or F. Advantageously, Z is $CF_3$ or $CF_2H$.

In an embodiment, all four of the X substituents are OR and, preferably, W is H. Advantageously, R is independently selected from the group consisting of $C(O)(CF_2)_5CF_3$, $C(O)(CF_2)_5CF_2H$ and $C(O)(CF_2)_6CF_3$.

In an even further embodiment, all four of the X substituents are OR, preferably W is H, wherein three of the R substituents are $C(O)(CH_2)_m(CF_2)_nY$ and the remaining R substituent is $CW_2C(CW_2OC(O)(CH_2)_m(CF_2)_nY)_3$. Preferably, m is and integer of 0 or 1, for example, 0. Favourably, n is an integer from 5 to 8, such as 5 or 6. Preferably, when m is 0, n is an integer of 5 or 6. Alternatively, when m is 1, n is an integer from 4 to 7. Preferably, Y is $C(Z)_3$, wherein, Z is advantageously H or F.

Advantageously, Z is $CF_3$ or $CF_2H$.

In a further embodiment, all four of the X substituents are OR, preferably W is H. Advantageously, three of the R substituents are independently selected from the group consisting of $C(O)(CF_2)_5CF_3$, $C(O)(CF_2)_5CF_2H$ and $C(O)(CF_2)_6CF_3$ and the remaining R substituent is independently selected from the group consisting of $CH_2C(COC(O)(CF_2)_5CF_3)_3$, $CH_2C(COC(O)(CF_2)_5CF_2H)_3$ and $CH_2C(COC(O)(CF_2)_6CF_3)_3$.

In some embodiments, the R groups of formula (I) may all be the same. In other embodiments, the R groups will be independently selected from the groups detailed above.

In an embodiment, the compound of formula (I) may have a structure according to formula (II), wherein R is $C(O)(CH_2)_m(CF_2)_nY$. Preferably, R may be independently selected from the group consisting of $—C(O)(CF_2)_5CF_3$, $—C(O)(CF_2)_5CF_2H$ and $—C(O)(CF_2)_6CF_3$.

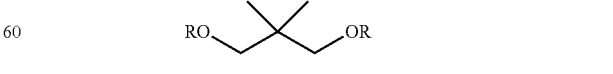

Formula (II)

In another embodiment, the compound of formula (I) may have a structure according to formula (III), wherein R is $C(O)(CH_2)_m(CF_2)_nY$. Preferably, R may be independently selected from the group consisting of $—C(O)(CF_2)_5CF_3$, $—C(O)(CF_2)_5CF_2H$ and $—C(O)(CF_2)_6CF_3$.

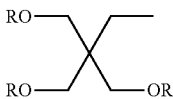

Formula (III)

In a further embodiment, the compound of formula (I) may have a structure according to formula (IV), wherein R is $C(O)(CH_2)_m(CF_2)_nY$. Preferably, R may be independently selected from the group consisting of —$C(O)(CF_2)_5CF_3$, —$C(O)(CF_2)_5CF_2H$ and —$C(O)(CF_2)_6CF_3$.

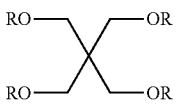

Formula (IV)

In an alternative embodiment, the compound of formula (I) may have a structure according to formula (IV), wherein three R substituents are $C(O)(CH_2)_m(CF_2)_nY$ and the remaining R substituent is $CW_2C(CW_2OC(O)(CH_2)_m(CF_2)_nY)_3$. Preferably, W is H. Advantageously, m is 0. Optionally, n is 5 or 6. Preferably, Y is $CF_3$ or $CF_2H$. Preferably, three of the R substituents are independently selected from the group consisting of —$C(O)(CF_2)_5CF_3$, —$C(O)(CF_2)_5CF_2H$ and —$C(O)(CF_2)_6CF_3$, and the remaining R substituent is chosen from the group consisting of —$CH_2C(CH_2OC(O)(CF_2)_5CF_3)_3$, —$CH_2C(CH_2OC(O)(CF_2)_5CF_2H)_3$ and —$CH_2C(CH_2OC(O)(CF_2)_6CF_3)_3$. To aid visually, substituting the portion of $CW_2C(CW_2OC(O)(CH_2)_m(CF_2)_nY)_3$ that is in parentheses with $CW_2OR'$, and making W equal to H, would result in R being independently selected from $C(O)(CH_2)_m(CF_2)_nY$ or $CH_2C(CH_2R')_3$. Therefore, in this embodiment where three R substituents are $C(O)(CH_2)_m(CF_2)_nY$, the remaining R substituent is $CW_2C(CW_2OC(O)(CH_2)_m(CF_2)_nY)_3$ and W is H, the compound of formula (I) may be represented by a structure according to formula (V).

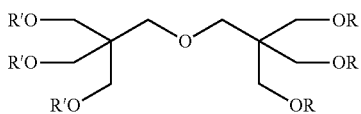

Formula (V)

In another aspect, the invention provides a lubricant composition comprising one or more compounds of formula (I). Preferably, the compound of formula (I) is in a proporation of at least 10 wt % to at least 50 wt % of the lubricant. More preferably, the compound of formula (I) comprises at least 80 wt % or 90 wt % of the lubricant.

In a further aspect of the invention, there is a provided a composition comprising a compound of formula (I).

In an embodiment, the composition may comprise at least two different compounds of formula (I). Preferably, the at least two different compounds may be present in the composition in a ratio of from around 1:10 to around 10:1, for example, 5-1:1-5.

The compounds of formula (I) are less flammable than polyalkylene glycol (PAG) and/or polyol ester (POE) based lubricants. Preferably, the compounds of formula (I) have a lowest temperature of ignition of about 500° C. or greater, such as 510° C., 520° C., 530° C., 540° C., 550° C., 560° C., 570° C., 580° C., 590° C., preferably about 600° C. or greater, for example 610° C., 620° C., 630° C. or 640° C.

Advantageously, the compounds of formula (I) have a high degree of miscibility with heat transfer fluids, particularly fluorine-based heat transfer fluids.

Preferably, the compounds of formula (I) will have a melting point of from about −20° C. to about −70° C., such as from about −25° C. to about −60° C., preferably from about −30° C. to about −50° C.

Preferably, the compounds of formula (I) will have a viscosity appropriate for use with heat transfer fluids, such as in refrigeration or air-conditioning devices. Conveniently, compounds of formula (I) with have a viscosity of from about 5 to about 220 cSt, such as from 10 to about 200 cSt, from about 15 to about 150 cSt or from about 20 to about 125 cSt. Preferably, the compounds of formula (I) will have a viscosity of from about 32 to about 100 cSt.

The compounds of formula (I) may be further used as heat transfer agents.

Compositions of the Invention

In another aspect, the invention provides a heat transfer composition, comprising a heat transfer portion together with one or more compounds of formula (I).

Such lubricant/heat transfer component compositions show low flammability, such as when sprayed onto hot surfaces or sprayed through a flame.

Preferably, the heat transfer portion comprises one or more compounds selected from the group of (hydro)fluoroolefins (HFOs), hydrofluorocarbons (HFCs), chlorofluorocarbons (CFCs), hydrochlorofluorocarbons (HCFCs) and hydrocarbons.

Advantageously, the heat transfer portion may comprise one or more compounds selected from the group of 1,3,3,3-tetrafluoropropene (R-1234ze), 2,3,3,3-tetrafluoropropene (R-1234yf), 3,3,3-trifluoropropene (R-1243zf), 1,1,1,2-tetrafluoroethane (R-134a), trifluoroethene (R1123), 1,1-difluoroethene (R-1132a), 1,1,1,4,4,4-hexafluorobutene (R1336mzz), 1,1-difluoroethane (R-152a), difluoromethane (R-32), fluoroethane (R-161), pentafluoroethane (R-125), 1,1,2,2-tetrafluoroethane (R-134), propane, propylene, carbon dioxide, 1,1,1,3,3-pentafluoropropane (R-245fa), 1,1,1,3,3,3-hexofluoropropane (R-236fa), 1,1,1,2,3,3,3-heptafluoropropane (R-227ea), 1,1,1-trifluoroethane (R-143a), n-butane, iso-butane and 1,1,1,3,3-pentafluorobutane (R-365mfc), such as R-1234ze, R-1234yf, R-1243zf, R-134a, R-152a and R-32.

For the avoidance of doubt, it is to be understood that where a compound may exist as one of two configurational isomers, e.g. cis and trans isomers around a double bond, the use of the term without an isomer designation (e.g. R-1234ze) is to refer to either isomer.

Conveniently, the heat transfer portion comprises tetrafluoropropenes. Preferably, the heat transfer portion comprises R-1234ze, even more preferably the heat transfer portion comprises R-1234ze(E). Advantageously, the heat transfer composition comprises R-1234yf.

Advantageously, compositions of the invention are less flammable than a composition comprising the same heat transfer portion combined with a polyalkylene glycol (PAG) and/or a polyol ester (POE) based lubricant.

Conveniently, the compositions of the invention are less flammable than the heat transfer portion alone.

Preferably, the composition of the invention has a lowest temperature of ignition of about 500° C. or greater, such as 510° C., 520° C., 530° C., 540° C., 550° C., 560° C., 570° C., 580° C., 590° C., preferably about 600° C. or greater, for example 610° C., 620° C., 630° C. or 640° C.

In an embodiment, the composition of the invention may be non-flammable.

Flammability may be determined in accordance with ASHRAE Standard 34 incorporating the ASTM Standard E-681 with test methodology as per Addendum 34p dated 2004, the entire content of which is incorporated herein by reference.

Conveniently, the Global Warming Potential (GWP) of the compositions of the invention may be less than about 3500, 3000, 2500 or 2000. For instance, the GWP may be less than 2500, 2400, 2300, 2200, 2100, 2000, 1900, 1800, 1700, 1600 or 1500. The GWP of the compositions of the invention preferably is less than 1400, 1300, 1200, 1100, 1000, 900, 800, 700, 600 or 500.

Preferably, the compositions of the invention have zero or near zero ozone depletion.

In an embodiment, the compositions of the invention have improved heat transfer properties than the heat transfer fluid alone.

Without wishing to be bound by theory, it is believed that compounds of formula (I) may further act as heat transfer agents and therefore increase the heat transfer properties of the compositions of the invention.

Advantageously, the composition further comprises a stabiliser.

Preferably the stabiliser is selected from group consisting of diene-based compounds, phosphates, phenol compounds and epoxides, and mixtures thereof.

Conveniently, the composition further comprises an additional flame retardant.

Preferably, the flame retardant is selected from the group consisting of tri-(2-chloroethyl)-phosphate, (chloropropyl) phosphate, tri-(2,3-dibromopropyl)-phosphate, tri-(1,3-dichloropropyl)-phosphate, diammonium phosphate, various halogenated aromatic compounds, antimony oxide, aluminium trihydrate, polyvinyl chloride, a fluorinated iodocarbon, a fluorinated bromocarbon, trifluoro iodomethane, perfluoroalkyl amines, bromo-fluoroalkyl amines and mixtures thereof.

The invention also provides a heat transfer device containing a composition of the invention and/or the use of a composition of the invention in a heat transfer device.

In an embodiment, the heat transfer device is a refrigeration device.

Conveniently, the heat transfer device is selected from the group consisting of automotive air conditioning systems, residential air conditioning systems, commercial air conditioning systems, residential refrigerator systems, residential freezer systems, commercial refrigerator systems, commercial freezer systems, chiller air conditioning systems, chiller refrigeration systems, and commercial or residential heat pump systems.

Preferably, the heat transfer device contains a compressor.

According to a further aspect of the invention, there is provided a method of cooling an article, which comprises condensing a composition of the invention and thereafter evaporating the composition in the vicinity of the article to be cooled.

According to an another aspect of the invention, there is provided a method for heating an article, which comprises condensing a composition of the invention in the vicinity of the article to be heated and thereafter evaporating the composition.

According to a further aspect of the invention, there is provided a mechanical power generation device containing a composition of the invention.

Preferably, the mechanical power generating device is adapted to use a Rankine Cycle or modification thereof to generate work from heat.

According to an another aspect of the invention, there is provided a method of retrofitting a heat transfer device comprising the step of removing an existing heat transfer fluid and introducing a composition of the invention. Preferably, the heat transfer device is a refrigeration device. Advantageously, the heat transfer device is an air-conditioning system.

According to a further aspect of the invention, there is provided a method of reducing the flammability of a composition by the addition of one or more different compounds of formula (I).

Methods of Preparation of Compounds and Compositions of the Invention

The invention provides a method of preparing a compound of formula (I) comprising reacting a compound of formula (A) with a compound of formula (B):

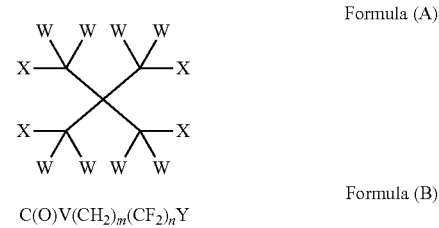

Formula (A)

$C(O)V(CH_2)_m(CF_2)_nY$

Formula (B)

wherein
W is independently selected from the group consisting of H, F, Cl, Br and I;
X is independently selected from the group consisting of H, F, Cl, Br, I, $CW_3$ and R, on the basis that at least one X is OR;
R is independently selected from the group consisting of H and $CW_2C(CW_2OH)_3$;
m is an integer from 0 to 2;
n is an integer from 2 to 8;
V is OH, F, Cl, Br or I;
Y is $C(Z)_3$; and
Z is independently selected from the group consisting of H, F, Cl, Br and I.

In an embodiment, in the compound according to formula (A), two of the X substituents are OR and the other two X substituents are H. Preferably, W is H. Advantageously, R is H.

In another embodiment, in the compound according to formula (A), three of the X substituents are OR and the other X substituent is $CW_3$. Preferably, W is H.

Advantageously, R is H.

In a further embodiment, in the compound according to formula (A), all four of the X substituents are OR. Preferably, W is H. Advantageously, R is H.

In another embodiment, in the compound according to formula (A), three of the X substituents are OR and the remaining X substituent is $CW_2C(CW_2OH)_3$.

Preferably, W is H. Advantageously, R is H.

In an embodiment, the compound according to formula (A) may be selected from the list consisting of pentaerythitol, trimethylopropane, di-pentaerythritol and neopentylene glcycol.

In an embodiment, in the compound according to formula (B), m is an integer of 0 or 1, for example 0. Favourably, n is an integer from 5 to 8, such as 5 or 6. Preferably, when m is 0, n is an integer of 5 or 6. Alternatively, when m is 1, n is an integer from 4 to 7. Preferably, Y is $C(Z)_3$, wherein, Z is advantageously H or F. Advantageously, Z is $CF_3$ or $CF_2H$. Preferably, V is Cl or Br.

In a further embodiment, the compound according to formula (B) may be selected from the list consisting of $CO_2H(CF_2)_5CF_3$, $CO_2H(CF_2)_5CF_2H$ and $CO_2H(CF_2)_6CF_3$.

In another embodiment, the compound according to formula (B) may be selected from the list consisting of $ClC(O)(CF_2)_5CF_3$, $ClC(O)(CF_2)_5CF_2H$ and $ClC(O)(CF_2)_6CF_3$.

In an embodiment, the method may proceed via the reaction of at least two different compounds of formula (A) with at least two different compounds of formula (B).

Preferably, the molar ratio of compound of formula (A) to compound of formula (B) is at least 1:2.

In some embodiments, the method is conducted in one-step reaction.

Compositions of the invention may be prepared by the method of mixing one or more compounds of formula (I) with a heat transfer fluid.

Compositions of the invention may be prepared by mixing one or more compounds of formula (I), prepared through a method of the invention, with a heat transfer fluid.

Preferably, the heat transfer fluid comprises one or more compounds selected from the group of (hydro)fluoroolefins (HFOs), hydrofluorocarbons (HFCs), chlorofluorocarbons (CFCs), hydrochlorofluorocarbons (HCFCs) and hydrocarbons.

Advantageously, the heat transfer fluid comprises one or more compounds selected from the group of R-1234ze, R-1234yf, R-1243zf, R-134a, R-152a, R-32, R-161, R-125, R-134, propane, propylene, carbon dioxide, R-245fa, R-236fa, R-227ea, R-143a, n-butane, iso-butane and R-365mfc.

Conveniently, wherein the heat transfer fluid comprises one or more compounds selected from the group of R-1234ze, R-1234yf, R-1243zf, R-134a, R-152a and R-32.

Preferably, the heat transfer fluid comprises R-1234ze.

Preferably, the heat transfer fluid comprises R-1234yf.

Compounds of Formula (I) may be provided by the following method. To a mixture of 6.7 g of trimethylolpropane and 62.1 g perfluoroocatanoic acid, heated to the melting point, 1 ml of sulphuric acid was added drop-wise, after which the heating was continued for 2 hours. The resulting mixture was washed with water, sodium carbonate solution and again dried with ware, dried over $CaCl_2$) and distilled in an oil pump vacuum.

An alternative method of making compounds of Formula (I) is as follows. 1.97 mmol of an acyl chloride and 0.66 mmol of a polyol were mixed in a round bottomed flask and heated at 70 to 150° C. for 12 hours. The solution was allowed to cool and the excess acid chloride was removed by distillation. The resulting compound was then optionally purified via silica gel chromatography.

A further alternative method of making compounds of Formula (I) is as follows. A 3-necked round bottom flask, fitted with a dropping funnel and a condenser, was flame dried and placed under a $N_2$ atmosphere. The alcohol was added to the round bottom flask at room temperature. The fluorinated or partially fluorinated acid chloride was dispensed in a glovebox and transferred to the alcohol via the dropping funnel at 0° C. The reaction mixture was then slowly heated to reflux and left until no further hydrogen chloride was evolved. The mixture was then distilled under vacuum.

Using this method a series of fluorinated polyesters were prepared, see Table 1.

TABLE 1

| Example | Structure |
|---------|-----------|
| 1 | $F_3C-(CF_2)_5-C(O)-O-CH_2-C(CH_3)_2-CH_2-O-C(O)-(CF_2)_5-CF_3$ |
| 2 | $F_3C-(CF_2)_5-C(O)-O-CH_2-C(CH_2CH_3)(CH_2-O-C(O)-(CF_2)_5-CF_3)_2$ with third branch $CH_2-O-C(O)-(CF_2)_5-CF_3$ |
| 3 | $HF_2C-(CF_2)_5-C(O)-O-CH_2-C(CH_2CH_3)(CH_2-O-C(O)-(CF_2)_5-CF_2H)_2$ with third branch $CH_2-O-C(O)-(CF_2)_5-CF_2H$ |
| 4 | $F_3C-CH_2-C(O)-O-CH_2-C(CH_3)_2-CH_2-O-C(O)-CH_2-CF_3$ |

Hot Manifold Testing

An assessment was made of the ease of ignition of the fluid of Example 4 when in contact with a hot metal surface, using the test apparatus and test method as described in ISO Standard ISO 20823:2003. In this test droplets of the fluid were allowed to fall vertically downwards onto an internally heated, cylindrical hot surface, inclined at a shallow angle to the horizontal, and which was additionally fitted with a horizontal gutter to trap liquid at one side of the cylindrical body. (The surface is hereinafter described as the "manifold").

The temperature of the manifold was increased stepwise until ignition was observed. Observations on the character and vigour of ignition were also recorded during each test. Five fluids of the invention, two PAG type lubricants (Nippon Denso ND12 and Daphne FD46XG, Comparative Examples 1 and 2 respectively) and one POE lubricant (Emkarate RL68H, Comparative Example 3) were tested.

TABLE 2

| Example | Highest temperature without ignition (° C.) | Lowest temperature with ignition (° C.) | Observations |
|---------|---------|---------|---------|
| 4 | 635 | 640 | 15 s delay before ignition |
| Comparative Example 1 | 438 | 443 | Immediate ignition; burning liquid collected |
| Comparative Example 2 | 462 | 467 | Immediate ignition; burning liquid collected |

TABLE 2-continued

| Example | Highest temperature without ignition (° C.) | Lowest temperature with ignition (° C.) | Observations |
|---|---|---|---|
| Comparative Example 3 | 628 | 633 | Immediate ignition; gas above tray also ignited by droplets |

As can be seen from the results above, it was found that the fluorinated species exhibited elevated combustion temperature compared to commercially available polyalkylene glycol (PAG) and polyol ester (POE) lubricant materials.

Preferences and options for a given aspect, feature or parameter of the invention should, unless the context indicates otherwise, be regarded as having been disclosed in combination with any and all preferences and options for all other aspects, features and parameters of the invention.

Where a molecule, for example HFO-1234ze, may take the form of E and Z isomers, the general disclosure of that molecule is intended to refer equally to both the E and Z isomers.

The invention is defined by the following claims.

The invention claimed is:

1. A heat transfer composition, comprising a heat transfer portion together with a lubricant portion comprising one or more compounds of formula (I):

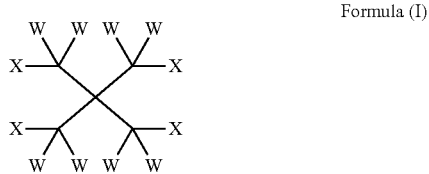

Formula (I)

wherein
W is independently selected from the group consisting of H, F, Cl, Br, and I;
X is independently selected from the group consisting of H, F, Cl, Br, I, $CW_3$, and OR on the basis that at least one X is OR;
R is independently selected from the group consisting of $C(O)(CH_2)_m(CF_2)_nY$ and $CW_2C(CW_2OC(O)(CH_2)_m(CF_2)_nY)_3$;
m is an integer from 0 to 2, provided that m is 1 or 2 if R is $C(O)(CH_2)_m(CF_2)_nY$;
n is an integer from 2 to 8;
Y is $C(Z)_3$; and
Z is independently selected from the group consisting of H, F, Cl, Br, and I.

2. A composition according to claim 1, wherein at least two or at least 3 of the X substituents are OR.

3. A composition according to claim 2, wherein the remaining X substituents are H.

4. A composition according to claim 2, wherein one X substituent is $CW_3$.

5. A composition according to claim 1, wherein R is $C(O)(CH_2)_m(CF_2)_nY$.

6. A composition according to claim 1, wherein when m is 0 and n is an integer from 5 to 8.

7. A composition according to claim 6, wherein when m is 0 and n is an integer of 5 or 6.

8. A composition according to claim 6, wherein Y is $CF_3$.

9. A composition according to claim 6, wherein Y is $CF_2H$ and m is 5.

10. A composition according to claim 1, wherein when m is 1 and n is an integer from 4 to 7.

11. A composition according to claim 1, wherein Y is independently selected from the group consisting of $CF_3$ and $CF_2H$.

12. A composition according to claim 1, wherein W is H.

13. A composition according to claim 1, comprising at least two different compounds of formula (I).

14. A composition according to claim 1, wherein the heat transfer portion comprises one or more compounds selected from the group consisting of (hydro)fluoroolefins (HFOs), hydrofluorocarbons (HCs), chlorofluorocarbons (CFCs), hydrochlorofluorocarbons (HCFCs), and hydrocarbons.

15. A composition according to claim 14, wherein the heat transfer portion comprises one or more compounds selected from the group consisting of R-1234ze, R-1234yf, R-1243zf, R1123, R-1132a, R1336mzz, R-134a, R-152a, R-32, R-161, R-125, R-134, propane, propylene, carbon dioxide, R-245fa, R-236fa, R-227ea, R-143a, n-butane, isobutane, and R-365mfc.

16. A composition according to claim 1, which is less flammable than a composition comprising the same heat transfer portion combined with a polyalkylene glycol (PAG) and/or polyol ester (POE) based lubricant.

17. A composition according to claim 1, wherein the lubricant portion is less flammable than the heat transfer portion.

18. A composition according to claim 1, which has an ignition temperature of about 500° C. or greater or which is non-flammable.

19. A composition according to claim 1 further comprising a stabiliser and/or an additional flame retardant.

20. A composition according to claim 19, wherein the stabiliser is selected from diene-based compounds, phosphates, phenol compounds and epoxides, and mixtures thereof.

21. A composition according to claim 19, wherein the flame retardant is selected from the group consisting of tri-(2-chloroethyl)-phosphate, (chloropropyl) phosphate, tri-(2,3-dibromopropyl)-phosphate, tri-(1,3-dichloropropyl)-phosphate, diammonium phosphate, various halogenated aromatic compounds, antimony oxide, aluminium trihydrate, polyvinyl chloride, a fluorinated iodocarbon, a fluorinated bromocarbon, trifluoro iodomethane, perfluoroalkyl amines, bromo-fluoroalkyl amines, and mixtures thereof.

22. A heat transfer device containing a composition according to claim 1.

23. A heat transfer device according to claim 22, which is a refrigeration device.

24. A heat transfer device according to claim 23, which is selected from the group consisting of automotive air conditioning systems, residential air conditioning systems, commercial air conditioning systems, residential refrigerator systems, residential freezer systems, commercial refrigerator systems, commercial freezer systems, chiller air conditioning systems, chiller refrigeration systems, and commercial or residential heat pump systems.

25. A method of cooling an article, which comprises condensing a composition according to claim 1 and thereafter evaporating the composition in the vicinity of the article to be cooled.

26. A method for heating an article, which comprises condensing a composition according to claim 1 in the vicinity of the article to be heated and thereafter evaporating the composition.

27. A mechanical power generation device containing a composition according to claim 1.

28. A mechanical power generating device according to claim 27, which is adapted to use a Rankine Cycle or modification thereof to generate work from heat.

29. A method of retrofitting a heat transfer device comprising the step of removing an existing heat transfer fluid and introducing a composition according to claim 1.

30. A method according to claim 29 wherein the heat transfer device is a refrigeration device.

31. A method according to claim 30 wherein the heat transfer device is an air-conditioning system.

32. A heat transfer composition, comprising a heat transfer portion together with a lubricant portion comprising one or more compounds of formula (I):

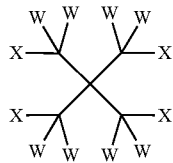

Formula (I)

wherein
W is independently selected from the group consisting of H, F, Cl, Br, and I;
all four of the X substituents are OR;
R is independently selected from the group consisting of $C(O)(CH_2)_m(CF_2)_nY$ and $CW_2C(CW_2OC(O)(CH_2)_m(CF_2)_nY)_3$;
m is an integer from 0 to 2;
n is an integer from 2 to 8;
Y is $C(Z)_3$; and
Z is independently selected from the group consisting of H, F, Cl, Br, and I.

33. A heat transfer device containing a composition according to claim 32.

34. A heat transfer device according to claim 33, which is a refrigeration device.

35. A heat transfer device according to claim 34, which is selected from the group consisting of automotive air conditioning systems, residential air conditioning systems, commercial air conditioning systems, residential refrigerator systems, residential freezer systems, commercial refrigerator systems, commercial freezer systems, chiller air conditioning systems, chiller refrigeration systems, and commercial or residential heat pump systems.

36. A method of cooling an article, which comprises condensing a composition according to claim 32 thereafter evaporating the composition in the vicinity of the article to be cooled.

37. A method for heating an article, which comprises condensing a composition according to claim 32 the vicinity of the article to be heated and thereafter evaporating the composition.

38. A mechanical power generation device containing a composition according to claim 32.

39. A mechanical power generating device according to claim 38, which is adapted to use a Rankine Cycle or modification thereof to generate work from heat.

40. A method of retrofitting a heat transfer device comprising the step of removing an existing heat transfer fluid and introducing a composition according to claim 32.

41. A method according to claim 40 wherein the heat transfer device is a refrigeration device.

42. A method according to claim 40 wherein the heat transfer device is an air-conditioning system.

43. A heat transfer composition, comprising a heat transfer portion together with a lubricant portion comprising one or more compounds of formula (I):

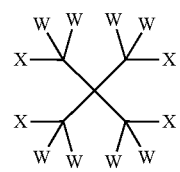

Formula (I)

wherein
W is independently selected from the group consisting of H, F, Cl, Br, and I;
X is independently selected from the group consisting of H, F, Cl, Br, I, $CW_3$, and OR on the basis that at least one X is OR;
R is independently selected from the group consisting of $C(O)(CH_2)_m(CF_2)_nY$ and $CW_2C(CW_2OC(O)(CH_2)_m(CF_2)_nY)_3$;
m is an integer from 0 to 2;
n is an integer from 2 to 8;
Y is $C(Z)_3$;
Z is independently selected from the group consisting of H, F, Cl, Br, and I; and
wherein one R substituent is $CW_2C(CW_2OC(O)(CH_2)_m(CF_2)_nY)_3$.

44. A composition according to claim 43, wherein three R substituents are $C(O)(CH_2)_m(CF_2)_nY$.

45. A heat transfer device containing a composition according to claim 43.

46. A heat transfer device according to claim 45, which is a refrigeration device.

47. A heat transfer device according to claim 46, which is selected from the group consisting of automotive air conditioning systems, residential air conditioning systems, commercial air conditioning systems, residential refrigerator systems, residential freezer systems, commercial refrigerator systems, commercial freezer systems, chiller air conditioning systems, chiller refrigeration systems, and commercial or residential heat pump systems.

48. A method of cooling an article, which comprises condensing a composition according to claim 43 thereafter evaporating the composition in the vicinity of the article to be cooled.

49. A method for heating an article, which comprises condensing a composition according to claim 43 the vicinity of the article to be heated and thereafter evaporating the composition.

50. A mechanical power generation device containing a composition according to claim.

51. A mechanical power generating device according to claim 50, which is adapted to use a Rankine Cycle or modification thereof to generate work from heat.

52. A method of retrofitting a heat transfer device comprising the step of removing an existing heat transfer fluid and introducing a composition according to claim 43.

53. A method according to claim 52 wherein the heat transfer device is a refrigeration device or an air-conditioning system.

54. A lubricant composition comprising a compound of formula (I) in a proportion of at least 10 wt % of the total weight of the lubricant:

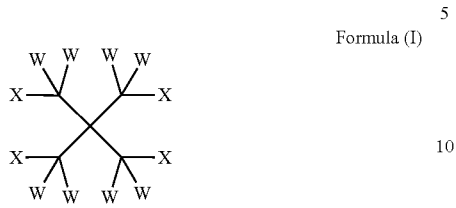

Formula (I)

wherein
W is independently selected from the group consisting of H, F, Cl, Br, and I;
X is independently selected from the group consisting of H, F, Cl, Br, I, $CW_3$, and OR on the basis that at least one X is OR;
R is independently selected from the group consisting of $C(O)(CH_2)_m(CF_2)_nY$ and $CW_2C(CW_2OC(O)(CH_2)_m(CF_2)_nY)_3$;
m is an integer from 0 to 2, provided that m is 1 or 2 if R is $C(O)(CH_2)_m(CF_2)_nY$;
n is an integer from 2 to 8;
Y is $C(Z)_3$; and
Z is independently selected from the group consisting of H, F, Cl, Br, and I.

\* \* \* \* \*

UNITED STATES PATENT AND TRADEMARK OFFICE
CERTIFICATE OF CORRECTION

PATENT NO. : 10,954,184 B2
APPLICATION NO. : 15/781415
DATED : March 23, 2021
INVENTOR(S) : Robert Elliot Low et al.

It is certified that error appears in the above-identified patent and that said Letters Patent is hereby corrected as shown below:

In the Claims

In Column 12, Claim 14, Line 15, delete "(HCs)" and insert in its place --(HFCs)--.

In Column 13, Claim 36, Line 53, insert --and-- between "32" and "thereafter".

In Column 13, Claim 37, Line 57, insert --in-- between "32" and "the".

In Column 14, Claim 48, Line 50, insert --and-- between "43" and "thereafter".

In Column 14, Claim 49, Line 54, insert --in-- between "43" and "the".

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*